United States Patent
Fischell et al.

(10) Patent No.: US 7,294,101 B2
(45) Date of Patent: *Nov. 13, 2007

(54) MEANS AND METHODS FOR TREATING HEADACHES

(75) Inventors: Robert E. Fischell, Dayton, MD (US); David R. Fischell, Fair Haven, NJ (US); Adrian R. M. Upton, Dundas (CA)

(73) Assignee: Neuropace, Inc., Mountain View, CA (US)

( * ) Notice: Subject to any disclaimer, the term of this patent is extended or adjusted under 35 U.S.C. 154(b) by 691 days.

This patent is subject to a terminal disclaimer.

(21) Appl. No.: 10/327,163

(22) Filed: Dec. 21, 2002

(65) Prior Publication Data

US 2004/0122281 A1 Jun. 24, 2004

(51) Int. Cl.
*A61N 2/04* (2006.01)
(52) U.S. Cl. .......................................... 600/13
(58) Field of Classification Search .............. 600/9–15; 607/1, 3, 45, 68, 71–72
See application file for complete search history.

(56) References Cited

U.S. PATENT DOCUMENTS 5,483,111 A * 1/1996 Kuznetsov ................. 310/12
5,725,471 A    3/1998 Davey et al.
6,132,361 A * 10/2000 Epstein et al. ............. 600/13
6,162,166 A * 12/2000 Neuwirth ................... 600/14
6,402,678 B1 * 6/2002 Fischell et al. ............ 600/13
2004/0138097 A1 * 7/2004 Guyuron ..................... 514/2

OTHER PUBLICATIONS

Barker, A.T. et al., "Non-Invasive Magnetic Stimulation of Human Motor Cortex," The Lancet, May 11, 1985, pp. 1106-1107.
Boroojerdi, M.D. et al., "Reduction of Human Visual Cortex Excitability Using 1-Hz Transcranial Magnetic Stimulation," Neurology, Apr. 2000, pp. 1529-1531.
Hallet, M., "Transcranial Magnetic Stimulation and the Human Brain," Nature, Jul. 13, 2000, vol. 406, pp. 147-150.

* cited by examiner

*Primary Examiner*—John P. Lacyk

(57) ABSTRACT

Disclosed is a system and method for treating headaches. The system employs a self-contained, battery operated, readily portable and easy-to-operate head-mounted magnetic depolarizer to generate a transient or time-varying high-intensity magnetic field into and around the user's head or neck. The magnetic depolarizer system can be used to depolarize the neurons of the brain and/or the trigeminal nerve. This type of neuronal depolarization has the capability for terminating migraine or other types of headaches.

28 Claims, 4 Drawing Sheets

MEANS AND METHODS FOR TREATING HEADACHES

FIELD OF USE

This invention is in the field of medical devices for the treatment of headaches by the application to the head and/or neck of magnetic field pulses.

BACKGROUND OF THE INVENTION

There are many types of headaches that afflict the human population. Migraine headaches cluster headaches, tension headaches and sinus headaches all cause serious pain and even disability. Moreover, migraine headaches occur in approximately 11% of the population in the U.S. and Western Europe each year, and more than 2.5 million persons in the U.S. have at least one day of migraine per week. Approximately 80 million additional people suffer from other types of severe headaches in the U.S. Although new drug therapies emerge each year, some patients cannot find relief with any existing drug therapy, and some therapies cause significant side effects. A non-invasive, non-drug method for preventing or treating migraine and other severe headaches would be a remarkable boon for those millions of people all over the world who suffer from these painful experiences.

Migraine is well known to be a neurovascular disorder that, in addition to pain, is characterized by autonomic nervous system dysfunction. Although the pain mechanisms are not well understood, it is believed that actions in nerves in the head, brainstem and other tissues cause blood vessels to dilate, which causes pain, which causes further nerve activation. In particular the trigeminal nerve and its associated autonomic nervous system function seem implicated in this process for migraine and cluster headaches. Disrupting this cycle can in some patients be a key to treating migraine and perhaps other forms of headache. It has also been demonstrated that magnetic (TMS) stimulation of the scalp causes alterations of the autonomic balance in the heart as measured by changes in the beat-to-beat variability of the heart.

Some patients with migraine experience a distinct aura or warning symptoms before the actual occurrence of the symptoms of the migraine headache. It is estimated that approximately 40% of all migraine patients have some type of aura that is a precursor of a migraine headache. Approximately half of these patients have a visual aura that typically begins as a small pattern of scintillating colored lights that have the appearance of wiggling worms or multicolored zigzags. Over a time period of between 20 and 30 minutes, the pattern enlarges and fades until it extends into the outermost portions of the visual field. During this time period, the patient might also completely lose part of his visual field. At the end of this visual aura, most migraine patients have a severe headache that is often accompanied by other symptoms such as nausea, vomiting and other unpleasant feelings. Many migraine patients who do not have a visual aura have some other precursor of a migraine that can be perceived from minutes to hours before the actual start of the headache. Special techniques may be used to treat patients with aura.

In 1985, A. T. Barker, et al (Lancet, 1985, pp. 1105-1107) described the use of an electromagnetic coil placed over the scalp which produced a high intensity, time varying, magnetic field. This magnetic field produces an electric current in the cortex of the human brain, which can in turn produce certain effects (e.g., depolarization and discharge) of brain neurons. This type of system has been given the name Transcranial Magnetic Stimulation (TMS). If repetitive magnetic pulses are applied in this manner, it has been given the name rTMS. In the journal Neurology (Apr. 11, 2000, pp. 1529-1531) it has been reported by B. Boroojerdi, et al, that rTMS at a rate of one pulse per second can create a reduction of the excitability of the neurons of the human visual cortex.

In U.S. Pat. No. 6,402,678, which is included herein by reference, Fischell et al. describe the use of one type of system for the prevention or treatment of migraine headaches using one or more high intensity magnetic pulses that depolarize the neurons of the cerebral cortex. However, the Fischell et al patent does not describe specific systems and methods for stimulation of the trigeminal nerve and its associated autonomic nervous system function. Furthermore, the Fischell et al patent makes no mention of stimulation of the neck or the use of a system that has one portion of the system located on the patient's head or neck that is connected to a separate power source by electrical wires.

SUMMARY OF THE INVENTION

The present invention is a system and method for treating and preventing headaches that includes a device for delivering one or more intense pulses of time-varying magnetic field to the head and/or neck of a person suffering from headache. In the preferred embodiment, this device is non-invasive, externally applied, portable, self-contained and under the control of the patient. The magnetic field pulses extend into the head and/or neck near the site where the device is applied in such a way that the local neurons are stimulated and depolarized. The present invention includes methods for using such a portable or non-portable device for treating a variety of types of headache. In one embodiment the time-varying magnetic field created by the system described above is sufficiently intense so as to penetrate the cranium and stimulate brain neurons and the wrappings or meninges of the brain; this device is called a Transcranial Magnetic Stimulator system (TMS). In another embodiment the time-varying magnetic field created by the system described above is less intense so that it can only penetrate the skin and other surface tissues of the face, head and/or neck and to stimulate surface nerves, such as the trigeminal nerve; this device is called a Transcutaneous Magnetic Stimulator (TcMS).

Recent literature in the field of neurology suggests that there is a correlation between the trigeminal nerve and headaches of various types. The trigeminal nerve is the large cranial (fifth) nerve that supplies sensation to the face, much of the scalp, meninges and the inside of the mouth. The trigeminal nerve also supplies motor nerve fibers for the muscles of the jaw. Preliminary laboratory experiments performed by Dr. Adrian Upton at McMaster University in Canada have indicated that Transcutaeous Magnetic Stimulation (TcMS) of the trigeminal nerve can reduce or eliminate headache pain in a majority of the patients who have been treated with this therapy. The advantage of TcMS compared to rTMS or TMS is that much less power is required to stimulate nerves located just below the skin (i.e., transcutaneously) than is required to generate significant electrical currents below the cranium and into the cerebral cortex. Therefore, one embodiment of the present invention is a means and method for stimulation of the trigeminal nerve and its branches by means of one or more magnetic pulses that act upon the neurons of the trigeminal nerve. Both TMS and TcMS systems are referred to herein as depolarizer systems. The depolarizer system is described as self-contained if it can be battery operated, and it is described as portable if it weighs less than 5 kg.

It should be noted that in the limited clinical study cited above, both TcMS and TMS have been successful in stopping headaches that had lasted for many hours and that were not successfully treated with medication. The present invention also includes the method of using a non-portable TMS or TcMS device to treat or prevent headaches.

One embodiment of this invention is a means and method for the treatment of migraine headaches for those patients who experience a distinct aura before the actual occurrence of the symptoms of the migraine headache. The visual aura is a result of the spatial progression of a band of brain cells that are excited in that band typically across one half of the brain's occipital lobe. This band moves in an anterior direction at the rate of approximately 2-5 mm per minute. It is believed that if the advancing band of excited neurons can be interrupted before the aura has completed its 20 to 30 minute time duration period, the migraine headache will not occur. One way to stop such an advancing band of excited brain neurons would be by imposing a high enough electric current through these neurons or neurons in the path of the advancing band so that they become depolarized and therefore they are not available to support the spread of the advancing band. One technique for electrically stimulating these neurons is by using a TMS device, alone or in combination with TcMS, that is placed over the occipital lobe of the brain so as to stimulate the neurons. These neurons would then be in a refractory state where they are less likely to participate in passing on the "aura" event. The device should be placed onto the patient's head as soon as possible after the patient becomes aware of a visual (or any other type) aura that is a precursor of a migraine headache. For patients whose aura originates from a region of the cerebral cortex other than the occipital lobe, the depolarizing device can be applied to the corresponding region of the head.

The one pulse per second of rTMS described by Boroojerdi, et al, which was proven to cause a reduction of cerebral cortex excitability, could be applied to break up the advancing band of excited neurons that is the cause of the visible aura of a migraine headache. Furthermore, a single TMS pulse or two to ten individual pulses spaced 2 to 100 seconds apart could also be used to depolarize the neurons of the cerebral cortex to stop an aura from proceeding to a full blown migraine headache.

The magnetic depolarizer system is expected to have a magnetic field generator, a control module with associated display devices, and a power module. The magnetic field generator is the source of the time varying magnetic field pulse. It includes an electromagnetic coil that is required to generate the magnetic pulses. It also typically contains the DC to DC converter and the capacitors that are discharged to provide the high level of electric current that is required to produce a high intensity magnetic field pulse. While other shapes are possible, the electromagnet can be formed in a racetrack, figure-eight shape, enclosed in an appropriate casing, and equipped with a holding means such as a Velcro strap, a handle or enclosed in a helmet. The length of the magnetic field generator would typically be between approximately 5 and 15 cm.

The power module would typically contain a rechargeable or replaceable (primary) battery to make the system self-contained and to help make the system portable. It would provide the variety of voltages needed for the system. The power system is expected to utilize a conventional AC adapter for providing direct power and/or for recharging the batteries. It would include the well-known capabilities of rechargeable systems such as low battery detection and safe recharging. The power module contains the circuitry needed to deliver power to the magnetic field generators capacitors.

The control module might be enclosed in the same housing as the magnetic field generator or it might be separate. It would typically contain the electronic devices needed to control the amplitude, number, frequency and duration of the magnetic pulses delivered by the device. In addition it would include the patient operated switch that is needed to turn the device on and off and deliver magnetic pulses. It would also include any display devices that would be needed by the patient to facilitate use of the TMS or TcMS system.

In one embodiment, the magnetic field generator, control module and power module are all contained in one unit called a single unit depolarizer. In another embodiment of the invention, the power module and portions of the control module are in one portion of the system that is connected to the magnetic field generator by electrically conducting wires. Thus the head unit portion of the device (which would be the magnetic field generator) would be smaller and lighter with at least some of the source for electric power being located remotely from the part of the system that is placed on the head. The portion of the system with the power module and all or part of the control module might be designed to sit on a table top and will be called the table top unit. Note that other embodiments are possible. The control module functionality can be split between the head unit and the tabletop unit in such a way as to minimize the weight of the head unit. In general it is expected that the on-off switch would be located on the tabletop unit and the pulse actuation switch could be located on the head unit.

Other embodiments of the device might include other divisions of functionality between the portion that is placed on the patient's head or neck and the portion that is in a separate unit.

Thus, an objective of this invention is to treat headaches, especially migraine headaches, by inducing a transient electrical current in a portion of the patient's cortex by applying a very strong magnetic field by means of a depolarizer system that includes a magnetic field generator placed close to or onto the head or neck.

Another objective of this invention is to treat headaches, especially migraine headaches, by inducing a small transient electrical current in a portion of the patient's trigeminal nerve and associated nerves by applying a strong magnetic field by means of a depolarizer system that includes a magnetic field generator placed close to or onto the head or neck.

Another objective of this invention is to prevent the occurrence of a migraine headache by creating a short duration, high intensity, time varying magnetic field by means of a magnetic depolarizer system whose magnetic field generator is placed onto the scalp of a patient who has an aura which is a precursor of a migraine headache, the magnetic field generator being adapted to cause depolarization of the neurons in the cerebral cortex where the aura originates.

Another object of this invention is to have the magnetic field generator placed by the patient onto his or her head or neck at a specific location relative to the patient's cerebral cortex, head or neck.

Still another object of the invention is to have a magnetic depolarizer system be self-contained and include a power module, a magnetic field generator, and control circuitry for creating a high intensity, time varying magnetic field, where settings of the system's operating parameters are preset by a physician or by the manufacturer and the system is operated by means of one or more patient operated switches.

Still another object of the invention is to have the magnetic depolarizer system be powered by a rechargeable battery.

Still another object of this invention is to have a self-contained magnetic depolarizer that can be held in the patient's hand and placed over a portion of the patient's head or neck to stimulate either or both the trigeminal nerve and the cerebral cortex with a time-varying magnetic field as a treatment for an ongoing headache.

Still another object of this invention is to have a self-contained device that provides a sufficiently high intensity, time-varying magnetic field pulse(s) to transcutaneously stimulate the trigeminal nerve, thereby providing a TcMS treatment for a headache.

Still another object of this invention is to have a portable, self-contained, magnetic depolarizer system that consists of a magnetic field generator adapted to be placed onto the patient's head by the patient and a power and control module connected by wires to the magnetic field generator, which power and control module provides the electrical power that is required to cause the magnetic field generator to generate a high intensity magnetic pulse.

Still another object of this invention is for the depolarizer system to be portable.

Still another object of this invention is for the depolarizer system to have a display to help the patient in the operation of the device.

Still another object of the invention is for the system to have control circuitry which creates a time delay between pulses administered by the patient.

Still another object of this invention is a method for using TMS or TcMS from a non-portable or a portable device for the treatment of a headache.

These and other objects and advantages of this invention will become obvious to a person of ordinary skill in this art upon reading the detailed description of this invention including the associated drawings as presented herein.

DETAILED DESCRIPTION OF THE INVENTION

Figure 1:
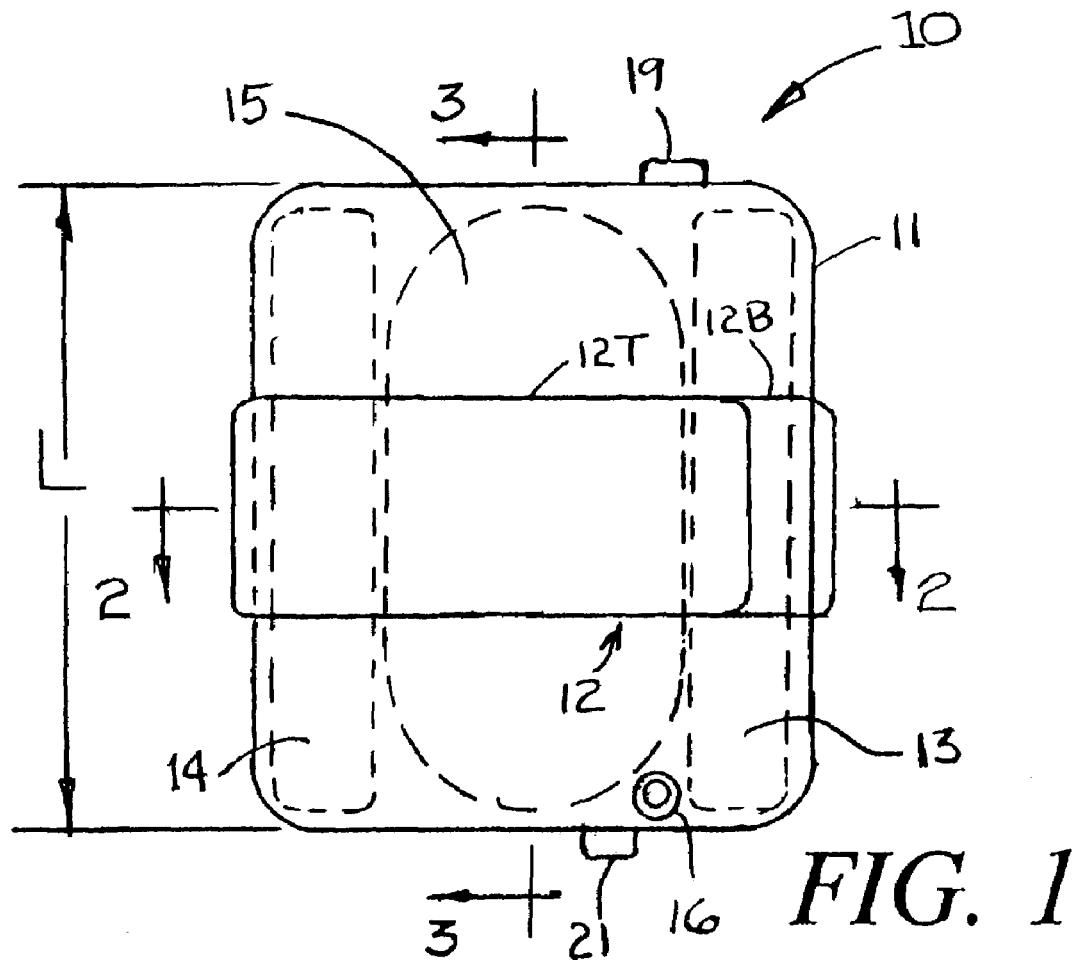
FIG. 1 is a top view of a single unit, self-contained, portable magnetic depolarizer system for the treatment of headaches.

FIG. 1 is a top view of a portable, self-contained, magnetic depolarizer 10 that has the capability to provide a high intensity magnetic field pulse (or train of pulses) for stimulation of the brain or for stimulation of the trigeminal nerve. Stimulation of the cerebral cortex of the brain will be referred to herein as TMS, and transcutaneous stimulation of the trigeminal nerve and of other surface nerves of the head and neck shall be referred to herein as TcMS. Both forms of stimulation can use the same type of device; e.g., any of the devices that are shown in FIGS. 1-8. However, TcMS stimulation of the trigeminal nerve requires much less power than the power required for stimulation of the brain by means of TMS. Therefore, the portion of the system that is to be placed on the patient's head can be smaller and lighter if only TcMS is to be applied.

Figure 5:
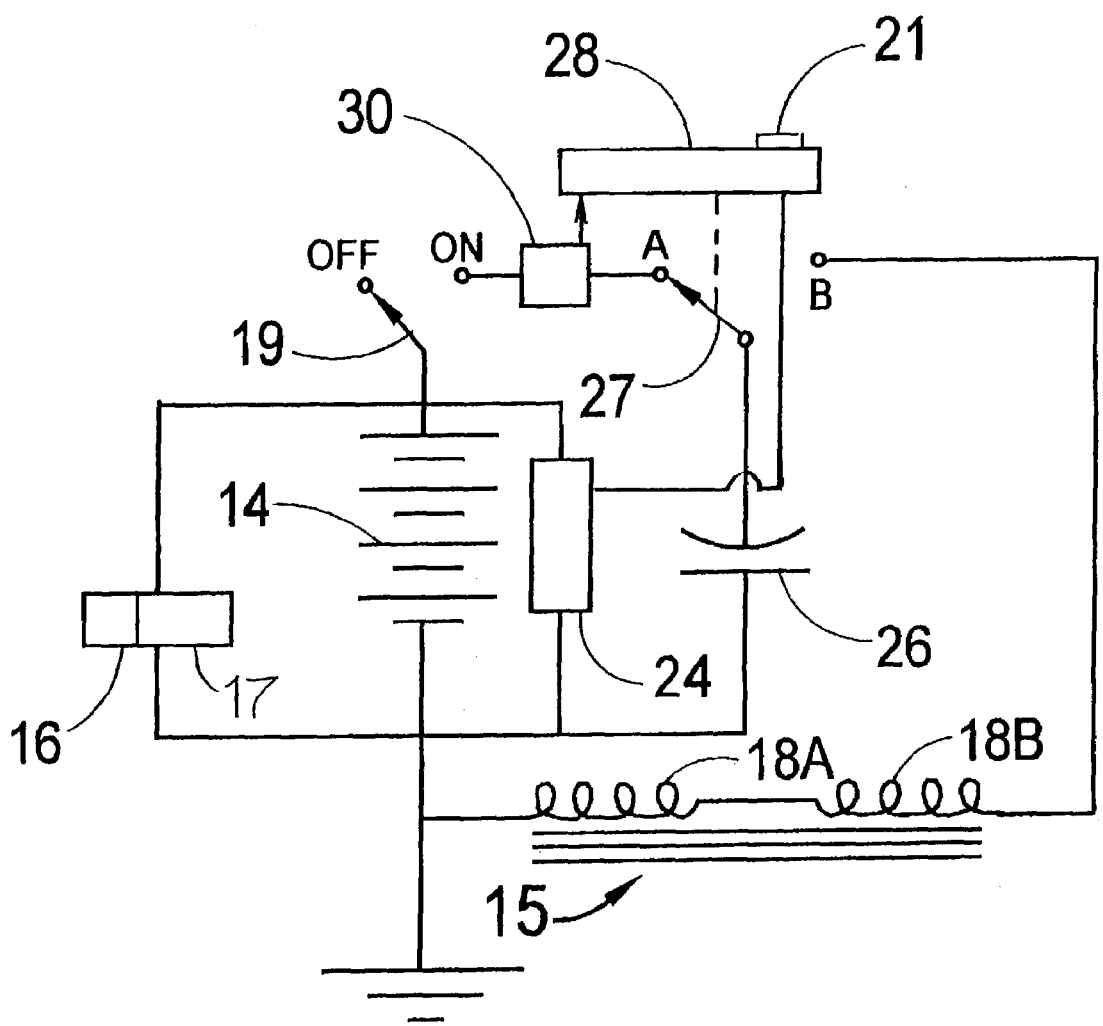
FIG. 5 is a block diagram of the electrical circuitry of the magnetic depolarizer of FIG. 1.

The depolarizer system 10 includes a case 11, a Velcro adjustable hand belt 12, an electronics module 13 that includes circuitry that implements power module functionality, magnetic pulse generator functionality and control functionality. The system 10 also includes a battery 14, an electromagnet 15, a recharging connector 16, an ON-OFF switch 19 and a magnetic level setting switch 21. FIG. 5 is a block diagram that illustrates the electrical connections between the electrical and magnetic components that are shown in FIG. 1. The length of magnetic field generator electromagnet 15 would typically be between approximately 5 and 15 cm. The width of the magnetic field generator might be between approximately 3 and 10 cm and its height in a direction above the skull (not including the Velcro hand belt 12) could be between approximately 1.0 and 5 cm.

Figure 2:
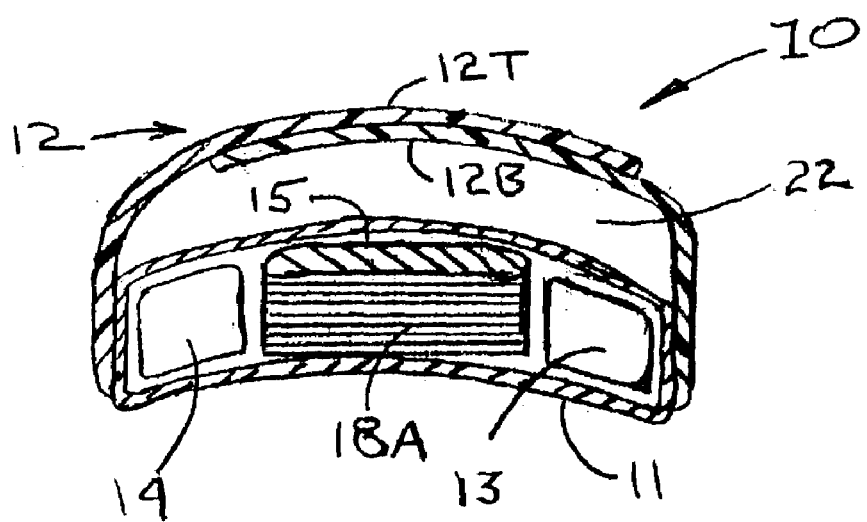
FIG. 2 is a cross section of the magnetic depolarizer at section 2-2 of FIG. 1.
Figure 4:
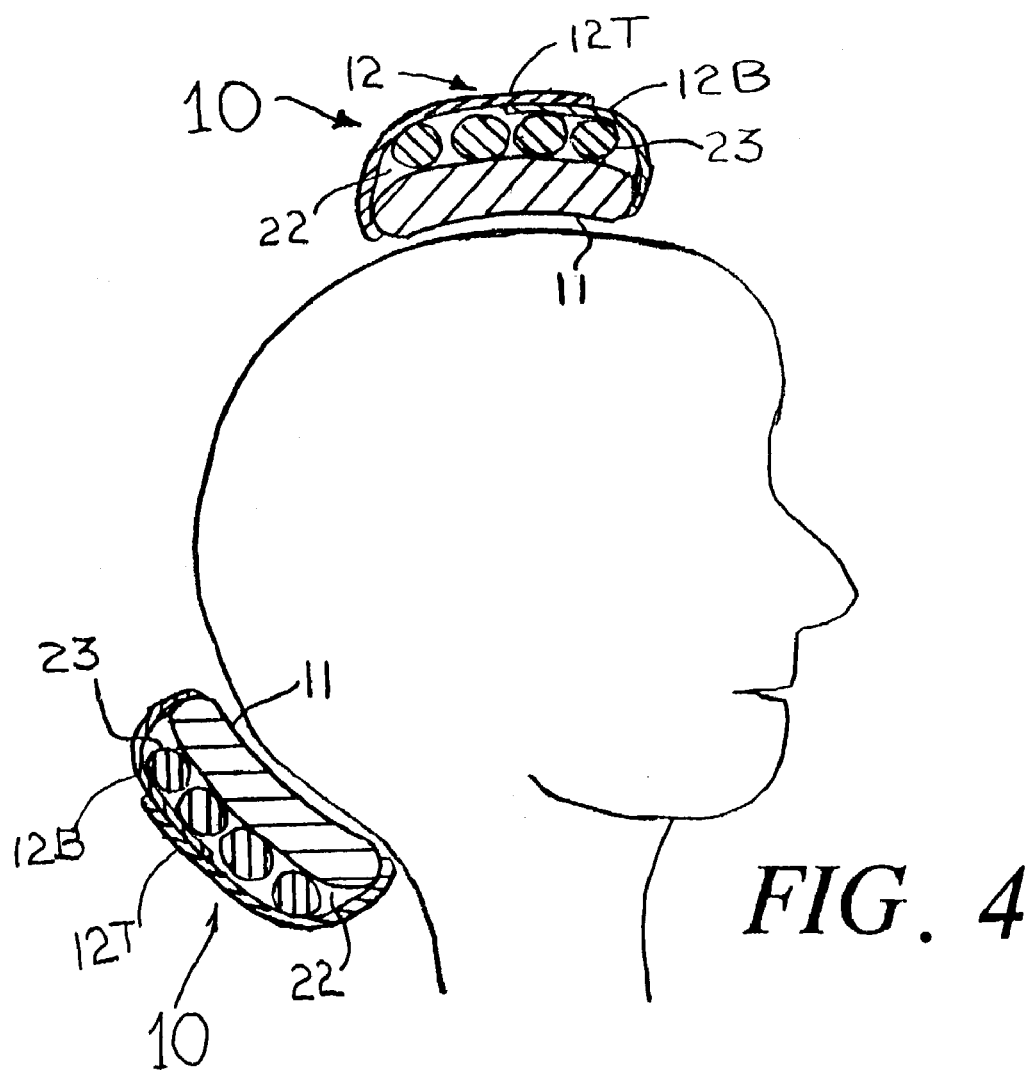
FIG. 4 illustrates two positions of the magnetic depolarizer on a patient's head or neck.

FIG. 2 is a cross section of the self-contained depolarizer 10 at section 2-2 of FIG. 1. The case 11 is preferably a plastic shell that contains all the parts of the depolarizer 10 except for the hand belt 12. The belt 12 consists of a top strap 12T and a bottom strap 12B; collectively being a Velcro adjustable hand belt 12. The two straps 12T and 12B are used by the patient to adjust the size of the hand hole 22 through which the patient's four fingers 23 are placed as shown in FIG. 4. Also shown in FIG. 2 are the electronics module 13, the battery 14 and the electromagnet 15 having a wire winding 18A.

Figure 3:
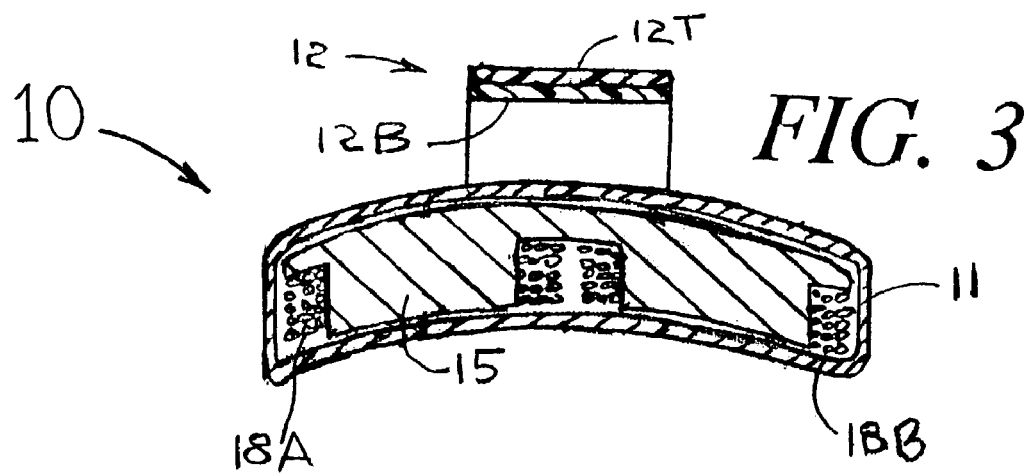
FIG. 3 is a cross section of the magnetic depolarizer at section 3-3 of FIG. 1.

FIG. 3 is a cross section of the magnetic depolarizer 10 at section 3-3 of FIG. 1. FIG. 3 shows the case 11, the belt 12 having top and bottom straps 12T and 12B respectively, the hand hole 22 and the electromagnet 15 having a first coil winding 18A and a second coil winding 18B. Although the electromagnet 15 could use an air core (i.e., a magnetic permeability of one) one preferred embodiment of the present invention uses a ferromagnetic core to enhance the generation of the magnetic field pulse. To reduce the magnetic energy lost in a magnetic pulse, the core of electromagnet 15 should be formed from a ferromagnetic material having a low hysteresis loss. A preferred version of the ferromagnetic core would be formed from thin laminations to decrease eddy current losses during the magnetic pulse. Optimally the ferromagnetic core would also have a high saturation flux density and high permeability to create the highest strength of the magnetic field with the lowest amount of energy. Such a ferromagnetic alloy would be selected from the group consisting of an iron-nickel alloy, a nickel-iron-molybdenum alloy, pure iron or other alloys of iron and/or nickel. An example of one such alloy is vanadium permendur. Also, it is envisioned to use either laminations of such alloys or powder metal cores or ferrite cores.

FIG. 4 illustrates two different positions for the magnetic depolarizer system 10 as placed onto the head or neck of a human subject. Shown in FIG. 4 are the cross sections of the human fingers 23 shown between the top of the case 11 and beneath the Velcro belt 12. It is expected that the four fingers 23, excluding the thumb, would be placed between the top of the case 11 and the belt 12. The top and bottom straps of the belt 12, i.e., the straps 12T and 12B respectively, would be adjusted by the patient so that his or her fingers 23 would fit snugly into the hand hole 22. It is also conceived that the magnetic depolarizer system 10 could have a handle (not shown) that would be held in the patient's hand as he or she places the device at some location that the patient has found to be effective in treating a headache. It will be recognized that either a handle or belt straps as described above, or a generic or patient-specific molded structure may be used as a positioner to ensure that the depolarizer is placed properly over the patient's trigeminal nerve. Other positioner structures are possible and will be apparent to a practitioner of ordinary skill in the art.

FIG. 5 is a block diagram of the magnetic depolarizer system 10. The rechargeable battery 14 can be recharged through the recharge control circuit 17 and receptacle 16 that can receive a plug from a conventional AC adapter (not shown) that transforms AC line voltage (e.g., 115 volts) to an appropriate DC voltage to recharge the rechargeable battery 14. An adapter for utilizing a car or boat 12-volt battery for operating the magnetic depolarizer system 10 is also envisioned. The recharge control circuit 17 provides well known power management capabilities of rechargeable systems such as preventing overcharge, detecting low battery voltage, allowing operation without battery when the recharger is available, and timers to automatically power off the system when appropriate.

When the patient is experiencing an aura of a migraine headache or experiencing a headache itself, he or she can throw the ON-OFF switch 19 to the ON position. That would cause the DC to DC converter 30 to come on and generate a high voltage for rapidly charging the capacitor 26. There would be a sufficient time delay (e.g., 3 to 10 seconds) between the time that the magnetic depolarizer system 10 is turned on and the time that the first magnetic pulse is generated to allow the patient to position the magnetic depolarizer on the head or neck. When the control circuitry 28 senses that the appropriate capacitor voltage has been reached, it moves the switch 27 from position "A" to position "B" thus discharging the capacitor 26 through the coils 18A and 18B of the electromagnet 15.

At the factory or under the control of a doctor a small number (typically one to five) combinations of pulse power, pulse train or single pulse and pulse train duration can be programmed into the control circuit 28. The treatment combination will be selected by the patient using selector switch 21. Once the system is powered on via switch 19 and the treatment combination is selected via switch 21, the control circuitry 28 will control switch 27 to deliver the desired pulse or pulse train. A two to four position switch 21 can be used to select from the preprogrammed menu the amount of energy stored in the capacitor 26 and to set a corresponding number of energy levels for the magnetic pulse. The switch 27 would typically be a solid-state controllable switch such as a thyristor that is capable of repeatable switching of a high electrical current in a few microseconds. As previously described, the coils 18A and 18B could have air cores or they could use a magnetically permeable core.

A sufficiently intense time-varying magnetic field pulse must be created that would cause neurons to be depolarized and thereby disrupt the start of a headache. For TMS, the intensity of the magnetic field at the surface of the brain should be between 0.1 and 5 Tesla. For TcMS the intensity of the magnetic field at 1 cm below the surface of the scalp should be between 0.1 and 5 Tesla. In both cases the pulse width of the magnetic pulse should be approximately between 0.1 and 5 milliseconds. The frequency rate of the magnetic pulses (if more than one is used) should be approximately between 0.1 Hz and 500 Hz. With some patients a single, short duration pulse may be all that is required. The magnetic pulses can be applied continuously for a period of between 0.1 and 50 seconds. By applying one or more magnetic field pulses to the neurons of the cerebral cortex and/or to the neurons in the scalp, many patients will be able to decrease the intensity and/or duration of a migraine headache.

The circuitry for the magnetic depolarizer system 10 can also include message circuitry 24 that can be used (as described in detail below) to inform the patient by audio or visual means how best to use the magnetic depolarizer system 10 for treatment of a headache.

Although FIGS. 1 and 4 show a magnetic depolarizer system 10 with a battery, the system 10 could also be operated by plugging into a receptacle at (typically) 115 or 230 volts AC. Such a system might or might not use a battery as part of its circuitry.

Figure 6:
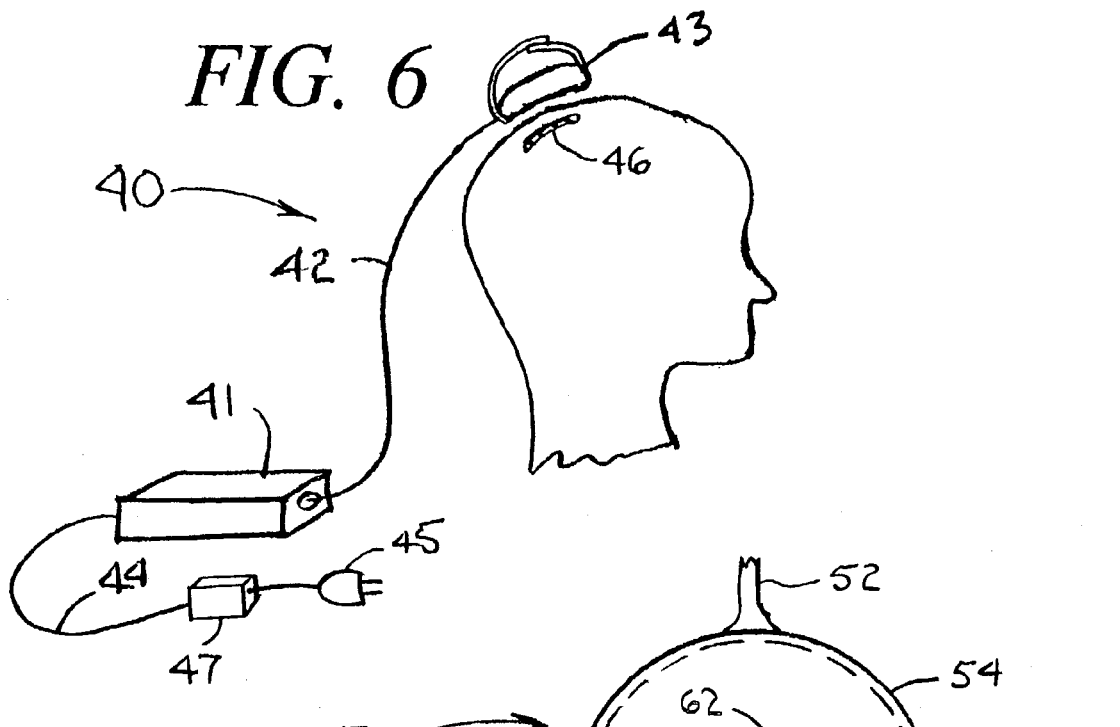
FIG. 6 is an alternative embodiment of the invention having a first part of the magnetic depolarizer which is a head unit that is a magnetic field generator designed to be placed on the patient's head or neck and a second part that is has power and control modules forming a tabletop unit that is connected by wires to the head unit.

FIG. 6 shows an alternative embodiment of a headache treatment system 40 that utilizes a tabletop unit consisting of a plug 45, a transformer 47 connected by the wire to the 44 to the power and control module 41. The tabletop unit is connected by an electrical wire cable 42 to the head unit which is the magnetic field generator 43. The magnetic field generator 43 would typically include the capacitor 26, the electronic switch 27 and the electromagnet 15 of FIG. 5. The power and control module 41 would typically include the battery 14, the ON-OFF switch 19, the DC to DC converter 30, the receptacle 16, the recharge control circuitry 17, message circuitry 24 and the part of the control circuitry 28 having a magnetic pulse energy adjustment switch 21. By having only the capacitor 14, electromagnet 15, part of the circuitry 28 to control the discharge of the capacitor 26 and the switch 27 in the magnetic field generator 43, its weight and size would be considerably reduced. Furthermore, the high current drawn by the windings 18A and 18B suggests that an optimum design has the shortest wire connections between the switch 27 and the capacitor 26. The energy lost by heating of the coils 18A and 18B can also be reduced by making the coils out of silver instead of copper or aluminum. Thus, the system 40 shown in FIG. 5 can be made to have the lighter and smaller part of the system be the head unit that is placed by the patient onto his or her head. Since the charging of the capacitor 26 would take place over a time period that is very long compared to the time period of discharge of the capacitor 26 into the coils 18A and 18B, the electric current flowing through the wire cable 42 is reasonably low. For example, if the capacitor 26 discharges an average of 4,000 amperes into the coils 18A and 18B in 0.5 milliseconds, and it takes 5 seconds to charge the capacitor, and if the efficiency of the process is 50%, then the current through the wire cable 42 is only 0.8 amperes. This comparatively low current can be carried by a copper wire cable 42 that would be comparatively light and flexible and would not develop any appreciable heating. For stimulating only the trigeminal nerve, a much lower level of current would typically be required.

It is envisioned that there are several other ways to distribute functionality between the power and control module and the head unit. For example, placing the switch 19 on the head unit or placing the DC to DC converter 30 in the head unit.

Also shown in FIG. 6 is a cross section of a thin sheet 46 of ferromagnetic material that could be surgically placed between the patient's cranial bone and the patient's trigeminal nerve. The depolarizer system could be used with or without ferromagnetic sheet 46. Such a ferromagnetic material sheet 46 would allow a much lower energy to be used for the magnetic pulse that causes depolarization of the trigeminal nerve. Examples of such a sheet of material would be 0.001 to 0.050 inches thick by approximately 0.1 to 2 inches wide and approximately 1 to 5 inches long and curved to fit snugly over the cranial bone. The ferromagnetic material would optimally have a relatively high permeability and high maximum flux density.

Also shown in FIG. 6 is a wire 44 and transformer 47 connected to a plug 45 for providing electric power for the power and control module 41. As stated previously, this recharger system could be used to recharge the batteries or to power the system without the battery in the circuit. The plug 45 could be used to connect to conventional line power (e.g., 115 VAC). Alternately cord 44 without the transformer 47 could be used to plug into a lighter receptacle of a car, or it could be used with any other appropriate source of electrical power. The power and control module 41 could use primary batteries such as one to four cells, or it could use rechargeable cells (e.g., nickel metal hydride or nickel cadmium cells). Warning lights on the power and control module 41 could be used to indicate when the battery is fully charged and/or when battery power is getting low.

Figure 7:
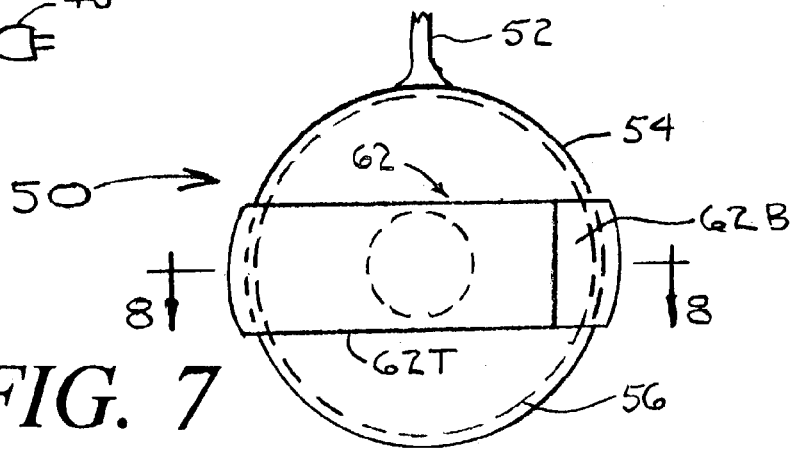
FIG. 7 is a top view of a magnetic depolarizer having an air core coil for creating the high intensity, time-varying magnetic field.

FIG. 7 is a top view of an alternative embodiment of the present invention that utilizes an air core electromagnet to generate the required magnetic field pulse. The magnetic field generator 50 of FIG. 7 would be connected to a power and control module (such as the power and control module 41 of FIG. 6) by means of a wire cable 52. Shown in FIG. 7 is the outline of an electromagnetic coil 56 within the magnetic field generator case 54. A belt 62 having top and bottom straps 62T and 62B respectively would be used to secure the magnetic field generator 50 around the patient's fingers or a handle could be provided.

Figure 8:
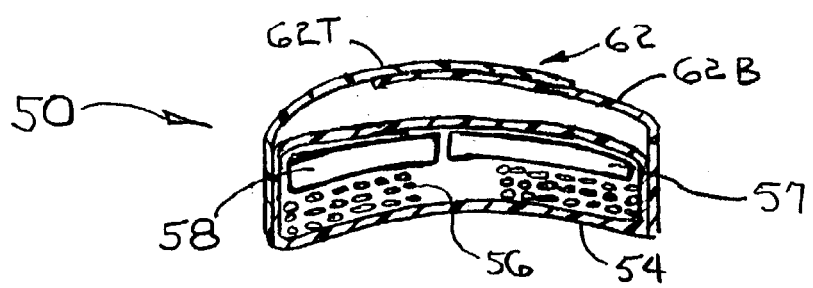
FIG. 8 is a cross section of the magnetic depolarizer at section 8-8 of FIG. 7.

FIG. 8 is a cross section of the magnetic field generator 50 at section 8-8 of FIG. 7. Shown in FIG. 8 are the case 54, the air core electromagnet 56, a capacitor 57, electronics module 58 and the Velcro belt 62 having a top strap 62T and a bottom strap 62B. It is also anticipated that the functionality of the power/control unit could be incorporated inside the case 54. In that case the depolarizer system would be contained in a single unit. The external wire connection would only be needed for recharging or for direct AC power.

It is also envisioned to have some portion of the system 10, 40 or 50 include electrical circuitry for providing audio and/or visual directions for the use of the magnetic depolarizer. These directions would typically be set up at the factory and could be a function of the setting of switch 21. Alternately it is envisioned that system directions and pulse definitions could be changed in the doctor's office by changing a ROM or similar device or by downloading instructions or data to a memory device. The message circuit 24 is envisioned to include one or more small speakers and screens to display status messages and instructions. The stored audio directions could be played through the speakers. The visual directions for use can also be stored in a memory chip and presented by an LCD message panel. The circuitry to provide such messages is represented by the message circuitry 24 in FIG. 5. Typical directions could include any one or all of the following statements: (1) "the system has been turned on," (2) "now place the head piece on your head," (3) "the first pulse has been delivered," (4) "the second (or third, fourth, etc.) pulse has been delivered," (5) "the last pulse has been delivered," (6) "the system is now turned off," (7) "the battery voltage is low, please recharge now," and (8) "your system is not operating properly, please consult the user's manual or call the phone number: 1-999-999-9999." Status lights could be used instead of or in addition to the visual/audio directions described above.

It should be understood that in order to be useful to a headache patient, the magnetic depolarizer system 10, 40 or 50 must have several distinct characteristics that are different from currently available systems for Transcranial Magnetic Stimulation (TMS). Specifically, the inventive concept of the present invention includes the fact that the magnetic depolarizer system 10 and the battery operated versions of the magnetic depolarizer systems 40 or 50 are readily portable, self-contained, have preset operating parameters that are not completely adjustable by the patient, can be placed on the patient's head by the patient and are turned on and off by the patient. "Self-contained" is defined herein as being battery operated. "Readily portable" can be defined as having a weight of less than 5 kg. The only presently known TMS equipment which is manufactured by the Cadwell company or the Magstim company is operated by a physician and not by a patient, has operational parameters that are continuously adjustable by the physician as it is being used (i.e., the parameters are not preset), has a magnetic coil that is placed on a patient by an attending physician, and since the entire system weighs well over 10 kg it is certainly not readily portable so as to be with the patient wherever he or she might need it.

To be most useful for its intended purpose, the magnetic depolarizer system 10 would have operating parameters that are preset by an attending physician using a ROM replacement strategy or any other well known means. These operating parameters can include one or more of the following attributes: the peak intensity of the magnetic field at a distance of 1.0 cm beneath the magnetic depolarizer; the time period of each magnetic pulse; the repetition rate of the magnetic pulses and the total number of pulses to be delivered when the magnetic depolarizer system is turned on. It should be understood that the TMS or TcMS device might have as many as four preset levels that the patient can select by means of the switch 21 located on a magnetic depolarizer. Once these parameters are set, the patient would operate the magnetic depolarizer system by placing it on his or her head and then turning the system on and then off after the headache has been treated. It is also envisioned that the system has only one operating level that is preset by the factory or by the patient's physician. It may be desirable for the patient to turn the system on but a timer would be used to automatically turn the system off after a preset period of time. The exact level of intensity of the magnetic field that would be set by the physician or by the patient would be determined by trial and error. That is, a level would be selected that provides the best and fastest relief for the patient as that patient would determine from the actual use of the magnetic depolarizer. That level may be reset from time-to-time as the results in stopping headaches indicates.

Since the aura of a migraine headache might occur at any time, and since the patient may have only 20 minutes to use the magnetic depolarizer system 10, each patient would want to have a system in relatively close proximity. For example, the patient would want to have the system at home, and/or at work, and/or in his or her car. The magnetic depolarizer system would optimally be sufficiently portable to be taken with the patient on a vacation or on a business trip.

It is also envisioned that the magnetic depolarizer system as described herein could be used for the treatment of other disorders such as depression, pain, epilepsy, bi-polar disease and other disorders of the brain.

Various other modifications, adaptations and alternative designs are of course possible in light of the teachings as presented herein. Therefore it should be understood that, while still remaining within the scope and meaning of the appended claims, this invention could be practiced in a manner other than that which is specifically described herein.

What is claimed is:

1. A magnetic depolarizer system for the treatment of a headache of a human subject, the system comprising:
    a readily portable magnetic depolarizer designed for placement at a specific location onto the head or neck of the subject, the magnetic depolarizer having at least one electromagnetic coil that is capable of providing a time varying magnetic field having a peak intensity at some portion of the subject's trigeminal nerve of at least 0.1 Tesla and a positioner configured to maintain the at least one coil in a desired position relative to the trigeminal nerve;
    electrical circuitry connected to the magnetic depolarizer for providing an electrical current through the at least one electromagnetic coil, the electrical circuitry also including a subject-operated switch for turning on the magnetic depolarizer system the system being turned off by a timing mechanism within the magnetic depolarizer system.

2. The system of claim 1 wherein the electrical circuitry of the magnetic depolarizer system includes a battery.

3. The system of claim 2 wherein the battery is rechargeable.

4. The system of claim 1 wherein the electromagnetic coil of the magnetic depolarizer has a core comprising a ferromagnetic material, the ferromagnetic material being selected from the group consisting of alloys of iron, alloys of nickel, iron-nickel alloys, iron-nickel-molybdenum alloys, vanadium permedur, a powder metal magnetic material, and a ferrite material.

5. The system of claim 4 wherein ferromagnetic material core is laminated to decrease the eddy current loss when creating the time-varying magnetic field.

6. The system of claim 1 wherein the electronic circuitry is adapted to deliver a plurality of time varying magnetic pulses.

7. The system of claim 6 wherein at least one pulse of the plurality of time varying magnetic pulses has a duration between approximately 0.1 and 5.0 milliseconds.

8. The system of claim 6 wherein the electronic circuitry is adapted to deliver a sequence of pulses at a rate of between approximately 0.1 Hz and approximately 500 Hz.

9. The system of claim 8 wherein the sequence of pulses is delivered over a time period of between approximately 0.1 second and approximately 50 seconds.

10. The system of claim 1, wherein the electrical circuitry is controlled by at least one operating parameter that is preset by a physician.

11. The system of claim 1 wherein the magnetic depolarizer system includes an instruction for informing the human subject on how to operate the magnetic depolarizer system.

12. The system of claim 11 wherein the instruction includes a message having a message type selected from the group consisting of an audio message type and a visual message type.

13. The system of claim 12 wherein the message includes at least one phrase selected from the group consisting of: "the system has been turned on," "now place the head piece on your head," "the first pulse has been delivered," "the second pulse has been delivered," "the last pulse has been delivered," "the system is now turned off," "the battery voltage is low, please recharge now," and "your system is not operating properly, please consult the user's manual or call a specified phone number."

14. The system of claim 1 further including a ferromagnetic piece placed between the cranial bone and the subject's scalp, wherein the ferromagnetic piece enhances the intensity of the time-varying magnetic field used to depolarize at least some of the neurons of the trigeminal nerve of the subject.

15. A method for the treatment of a headache, the method comprising the following steps:
    using a positioner to maintain a magnetic field generator onto the head or neck of a subject suffering from, or about to suffer from, a headache in a desired position relative to the subject's trigeminal nerve, by the subject himself or herself, the placement being at a location where the magnetic field generator can create at least one magnetic field pulse that has sufficiently high magnetic field intensity for depolarization of at least some neurons of the trigeminal nerve.

16. The method of claim 15 further comprising the step of turning the magnetic field generator on to create a plurality of time-varying magnetic pulses at the patient's trigeminal nerve.

17. The method of claim 15 further comprising the step of applying a plurality of magnetic pulses at a rate between approximately 0.1 Hz and approximately 500 Hz.

18. The method of claim 15 comprising the step of applying a sequence of magnetic pulses for a time period between approximately 0.1 second and approximately 50 seconds.

19. The method of claim 15 further comprising the step of applying at least one of the sequence of magnetic pulses having a duration between approximately 0.1 and 5 milliseconds.

20. The method of claim 15 further comprising the step of applying power to the magnetic field generator with a rechargeable battery.

21. The method of claim 15 further comprising the steps of causing the subject to turn an ON-OFF switch first to the ON position and subsequently causing the subject to turn the switch to the OFF position.

22. The method of claim 15 further comprising the steps of causing the subject to turn an ON-OFF switch to the ON position and subsequently automatically deactivating the magnetic field generator after a time period.

23. The method of claim 15 further comprising the step of causing a physician to set at least one operating parameter of the magnetic field generator.

24. A method for using a magnetic depolarizer system to treat a headache in a subject in need thereof, the method comprising:
    detecting an occurrence of a headache;
    activating the magnetic depolarizer system; and generating a time-varying magnetic field having a peak intensity at some portion of the patient's trigeminal nerve of at least 0.1 Tesla.

25. The method of claim 24 wherein the magnetic depolarizer system is readily portable and self-contained.

26. The method of claim 24, wherein the step of detecting the occurrence of a headache comprises receiving an input from the patient.

27. A self-contained, battery-operated system for reducing the intensity and/or duration of a headache by applying a time-varying magnetic field for transcutaneous magnetic stimulation of the trigeminal nerve of a human subject, the system having an electromagnetic coil designed to create a peak magnetic field intensity of at least 0.01 Tesla when measured below the surface of one of the scalp or the skin of the neck proximate to the trigeminal nerve.

28. A magnetic depolarizer system for providing transcutaneous magnetic stimulation of the trigeminal nerve of a human subject, the system having a first portion that is adapted to be positioned external to the patient and is capable of generating one or more magnetic pulses and a second portion formed at least in part of a ferromagnetic material that is adapted to be positioned under the skin or scalp of the patient; wherein the second portion will enhance the intensity of any magnetic pulse that is generated by the first portion.

\* \* \* \* \*